United States Patent [19]

Lombardo et al.

[11] 4,318,481
[45] Mar. 9, 1982

[54] METHOD FOR AUTOMATICALLY SETTING THE CORRECT PHASE OF THE CHARGE PULSES IN AN ELECTROSTATIC FLOW SORTER

[75] Inventors: Igino Lombardo, Sharon; Donald E. Barry, Norwood, both of Mass.

[73] Assignee: Ortho Diagnostics, Inc., Raritan, N.J.

[21] Appl. No.: 68,234

[22] Filed: Aug. 20, 1979

[51] Int. Cl.³ .............................................. B07C 5/342
[52] U.S. Cl. ................................. 209/3.1; 209/579;
 209/906; 250/222 PC; 346/75; 356/72;
 361/226; 364/413
[58] Field of Search .................................. 209/3.1–3.3,
 209/571, 579, 906, 127 R; 250/222 R, 222 PC;
 356/39, 72, 73, 335, 338; 361/226; 364/413;
 346/75

[56] References Cited

U.S. PATENT DOCUMENTS

| | | | |
|---|---|---|---|
| 3,380,584 | 4/1968 | Fulwyler | 209/3 |
| 3,710,933 | 1/1973 | Fulwyler et al. | 209/3.1 |
| 3,710,933 | 1/1973 | Fulwyler et al. | 209/3 |
| 3,761,941 | 9/1973 | Robertson | 346/1 |
| 3,769,627 | 10/1973 | Stone | 346/75 |
| 3,826,364 | 7/1974 | Bonner et al. | 209/3.1 |
| 3,826,364 | 7/1974 | Bonner et al. | 209/3 |
| 3,836,912 | 9/1974 | Ghougasian et al. | 346/75 |
| 3,851,169 | 11/1974 | Faxvog | 250/222 |
| 3,878,519 | 4/1975 | Eaton | 346/1 |
| 3,907,429 | 9/1975 | Kuhn et al. | 356/72 |
| 3,920,702 | 10/1975 | Corll | 356/72 |
| 3,941,479 | 3/1976 | Whitehead | 356/102 |
| 3,953,860 | 4/1976 | Fujimoto et al. | 346/75 |
| 3,963,606 | 6/1976 | Hogg | 209/3 |
| 3,982,251 | 9/1976 | Hochberg | 346/1 |
| 4,025,926 | 5/1977 | Fujimoto et al. | 346/1 |
| 4,045,770 | 8/1977 | Arnold et al. | 346/75 |
| 4,047,183 | 9/1977 | Taub | 346/1 |
| 4,047,183 | 9/1977 | Taub | 346/1 |
| 4,148,718 | 4/1979 | Fulwyler | 209/3.1 |
| 4,148,718 | 4/1979 | Fulwyler | 209/3.1 |

OTHER PUBLICATIONS

Chen et al., "Feedback for Synchronized Pressure Jet using Optical Sensor", IBM Tech. Discl., vol. 16, No. 12, 5/74.

"Laser Flow Microphotometry for Rapid Analysis and Sorting of Mammalian Cells", Mullaney, et al., Annals New York Academy of Sciences, vol. 267, pp. 176–190.

"Feedback for Syncronized Pressure Jet Using Optical Sensor", IBM Technical Disclosure Bulletin, vol. 16, No. 12, May 1974, pp. 3877–3878.

"Phase Detection on Ink Jet Droplets", IBM Technical Disclosure Bulletin, vol. 16, No. 3, Aug. 1973, p. 880.

*Primary Examiner*—Joseph J. Rolla
*Attorney, Agent, or Firm*—Audley A. Ciamporcero

[57] ABSTRACT

In order to initiate the charging of droplets at a specific point in time with respect to the formation of those droplets in an electrostatic flow sorting system, the charge phase of the system of the present invention is continuously and automatically adjusted by droplet break point monitoring. The charge phase is therefore flow rate and fluid velocity independent. The break point is monitored by a light source which is focused onto the jet stream at the droplet formation break point, or close to it, and the modulation of light caused by the scatter induced by the sheath stream portion as it passes the focused beam of light is detected via the use of a suitable electro-optical detector. From the output of the electro-optical detector, after appropriate signal conditioning, an electrical wave form is obtained which shape depends upon the shape of the fluid column passing the focus beam. Using this conditioned detector output, the charge pulse phase is automatically controlled to occur at a set point in time with respect to a transition point on the waveform thus obtained. Additionally, in order to compensate for large flow rate variations, the focused beam detector can be automatically repositioned to track with the breakpoint. The correct phase of the charge pulse will accordingly continue to be derived from the breakpoint electrical waveform. Alternatively, by monitoring the jet stream at points above or below the breakpoint, the phase adjustment is possible, however, somewhat fluid velocity dependent.

16 Claims, 1 Drawing Figure

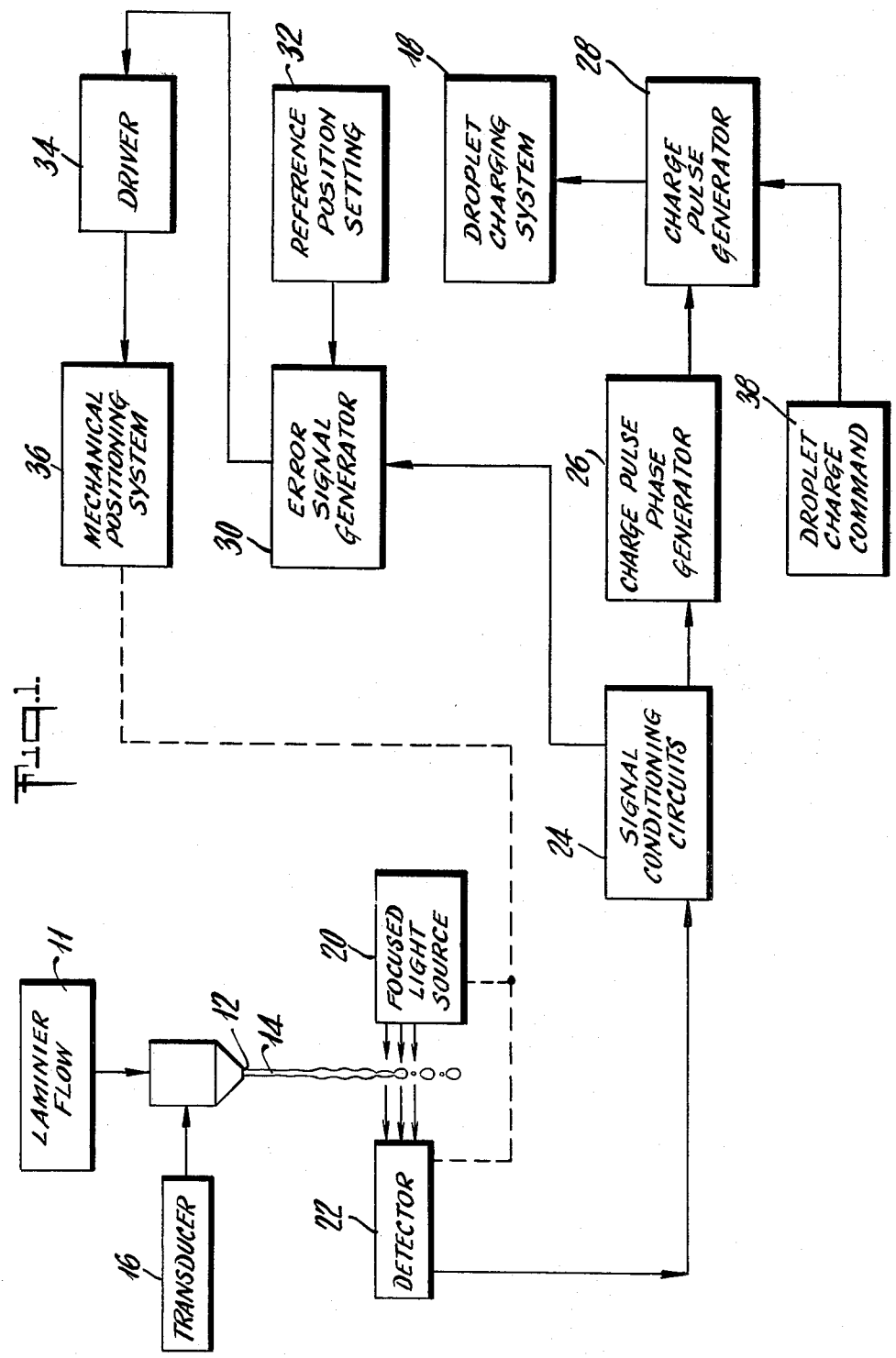

METHOD FOR AUTOMATICALLY SETTING THE CORRECT PHASE OF THE CHARGE PULSES IN AN ELECTROSTATIC FLOW SORTER

CROSS REFERENCE TO RELATED APPLICATIONS

The present application is related to the following applications, each of which is assigned to the assignee of the present application and are hereby incorporated by reference as if fully set forth herein: The invention of Igino Lombardo, Donald E. Barry, and W. Peter Hansen entitled, "Method For Detecting And Controlling Flow Rates Of The Droplet Forming Stream Of An Electrostatic Particle Sorting Apparatus", Ser. No. 68,231, filed Aug. 20, 1979; the invention of Igino Lombardo and W. Peter Hansen entitled, "Method And Apparatus For Positioning The Point Of Droplet Formation In The Jetting Fluid Of An Electrostatic Sorting Device", Ser. No. 68,113, filed Aug. 20, 1979; the invention of Igino Lombardo and Donald E. Barry entitled, "Automatic Relative Droplet Charging Time Delay System For An Electrostatic Particle Sorting System Using A Relatively Moveable Stream Surface Sensing System", No. 68,259, filed Aug. 20, 1979; the invention of Donald E. Barry and Igino Lombardo entitled, "A Method For Measuring The Velocity Of A Perturbed Jetting Fluid In An Electrostatic Particle Sorting System", Ser. No. 68,235, filed Aug. 20, 1979; and the invention of Richard A. Dussault and Igino Lombardo entitled, "A Servo System To Control The Spatial Position Of Droplet Formation Of A Fluid Jet In A Cell Storing Apparatus", Ser. No. 68,112, filed Aug. 20, 1979.

BACKGROUND OF THE INVENTION

The present invention relates generally to the field of electrostatic flow sorters, and more particularly to those sorters which are adapted to sense the presence and/or character of particles in a laminar flow stream and to selectively sort those particles by breaking that stream into a number of discrete droplets, and sorting those droplets containing such preselected particles. Such sorters are known for use in sorting and analyzing cellular compositions of given biological samples, as for example in the counting/analysis of cell types for a given blood sample.

In an apparatus of this general type, laminar flow is established through an area at which a light scattering, florescence or volume measurement is taken. Once a cell of interest has been sensed, an electronic time delay is normally activated for the length of time required for the cell to cover the distance from the point of cell detection to the point of droplet formation. Droplet formation may be accomplished by vibrating a flow chamber or orifice through which the stream passes, at a frequency sufficient to cause droplet formation, usually on the order of about 40,000 cycles per second. When a cell of interest arrives at the droplet formation point, a charging pulse may be applied to charge the droplet (plus, minus, or neutral) so that as the droplet of interest enters a subsequent DC field, it may be deflected as desired for collection. A general overview of this technique is provided in "Laser Flow Microphotometry For Rapid Analysis And Sorting Of Mammalian Cells", Mullaney, et al, Annals New York Academy Of Sciences, Vol. 267, pages 176-190 (see in particular, pages 180 and FIGS. 3 and 4).

Such particle sorters are also disclosed in U.S. Pat. Nos. 3,710,933 (Fulwyler, et al) and 3,380,584 (Fulwyler) and 4,148,718 (Fulwyler). In these patents, sorting is accomplished in accordance with a selected parameter which may be size, volume, presence of radioactivity, color, florescence, light absorption or any quality capable of being translated into an electrical quantity. These patents additionally disclose single or multi parameter measurements to effect such sorting.

In order to selectively sort those droplets containing cells which are determined to be of particular interest, apparatus of this general type generally depends upon a flow rate estimate for the fluid containing a particular cell. This flow rate estimate is used to estimate the time between cell detection and the droplet breakpoint, at which selective charging of the droplet to be sorted takes place. As disclosed in U.S. Pat. No. 3,710,933, such systems are normally aligned and adjusted prior to taking cell measurements. In particular, droplet formation is normally checked by illuminating the emerging liquid jet near the flow chamber with a strobe light or equivalent light source. The strobe light is synchroflashed with respect to the oscillator frequency. Droplet formation can then be viewed using a microscope, and by varying the voltage and frequency applied to the stream perturbing transducer, droplet formation can be adjusted for a given nozzle diameter and flow rate. See U.S. Pat. No. 3,710,933, Column 11, lines 14-49.

As described particularly in U.S. Pat. No. 3,710,933, (Fulwyler, et al), by pressurizing various reservoirs with known pressures, flow rates can be estimated and cell flow rate adjusted by varying the relative pressures between the various reservoirs feeding into the flow stream. The approximate time delay between cell sensing and droplet formation (which is estimated in Fulwyler, et al to be in the order of 1400 microseconds) can be estimated so that an appropiate droplet charging generator will operate in combination with a pulse height analyzer and cell separation logic to charge the selected cell containing droplets for subsequent electrostatic sorting.

A number of factors affect the ability of a given apparatus to selectively sort one or more types of target cells from a continuous cell stream. Even assuming that the detection equipment for identifying each cell to be sorted in 100% accurate, differences in flow rate, temperature, fluid viscosity, and transducer performance can effect the time delay or location of the desired target-cell-containing droplets at the breakpoint, which is the point at which a charge pulse must be administered to insure that the target cell will be subsequently electrostatically sorted.

Heretofore, one of the methods used to adjust such a sorting apparatus involves running a test sample through that apparatus which is set or programmed to sort for one or more readily identifiable cell types. According to this procedure, the delay time is manually adjusted until those droplets which are sorted from the flow stream are found to contain the expected number of target cells. While this method, used alone or in combination with the stroboscopic method discussed above, has achieved some success in this art, it is prone to a certain degree of error, particularly during periods of extended machine use and/or changing operating conditions, such as changing sample viscosities and/or temperatures.

In U.S. Pat. No. 3,826,364 (Bonner, et al), a particle sorting method and apparatus are disclosed wherein a coaxial flow stream is released through a vibrating nozzle. Inspection (interrogation) of the stream by one or more cell sensing means for sensing cells in the stream occurs immediately downstream of the nozzle. In the Bonner, et al device, charging pulses are supplied at appropriate times for proper separation of the drops through the use of delay units which are ajusted to provide the necessary time delay to allow for travel time of the particle from the point of particle scatter detection to the point where the stream breaks into drops. Bonner states:

"With the present arrangement the delay time between the observation of a particle and its capture by a separating droplet is predictable to within three drop periods. Such high degree of predictability is due primarily to the uniform velocity of the inner particle containing stream 12A of the coaxial flow jet. That is, across the inner stream 12A the stream velocity is substantially uniform whereby particles anywhere within the cross-section of the inner stream travel with the same velocity from the point of observation to the drop separation point of the stream." U.S. Pat. No. 3,826,364, Col. 7, lines 22-32.

As further explained in the Bonner, et al disclosure, the duration as well as the time of application of the charging pulse is critical to the separation of at least the droplet containing the target particle to be sorted. After describing a preferred charging pulse which will charge at least three drops, Bonner, et al states:

"Obviously, if instrument tolerances variations, drift and like permitted, then a drop charging time sufficient to charge only two successive drops, or a single drop, could be employed." U.S. Pat. No. 3,826,364, Col. 8, lines 2-6.

As also pointed out by Bonner, et al, a drop breaking from a given flow stream carries with it a charge which is proportional to the potential between the droplet stream and the surrounding electrodes or charging surfaces at the time the drop separates from the stream. If the drop breaks off from the jet stream during the transition time from the drop charge pulse, either during the leading or trailing edge of that pulse, some intermediate value between zero and the desired full charge may be imparted to the target droplet. In the Bonner, et al apparatus, on/off transitions of the drop charging pulse are synchronized with the drop formation means, whereby charge pulse transitions may be synchronized to occur only intermediate the formation of droplets and not when droplets separate from the stream. This is made possible in the Bonner device by the provision of a variable phase control unit included in the transducer drive circuit which is adjusted for proper timing of droplet formation with the droplet charge pulse. As with the Fulwyler devices discussed above, stroboscopic illumination of the stream permits stream viewing through a suitable microscope, the stroboscopic illumination being synchronized by the drop charging pulses such that the stream, and more particularly the defleted drops, may be illuminated to ensure that the deflected drops contain the desired particles to be sorted.

More recently, various apparatus and method have been proposed for timing the application of a charge pulse so that droplets containing the particles to be sorted may be selectively charged. In U.S. Pat. No. 3,963,606 (Hogg), a particle separator is disclosed for separating particles in a fluid according to certain particle characteristics. The Hogg device includes a means for adjusting an electrical delay to be equal to the time between the emergence of a particle from a jet forming aperture to the point of break off. Hogg proposes the use of a movable scale in place of the ground glass of prior art projection microscopes, this scale being linked to a potentiometer of an RC oscillator to thereby control the oscillator's frequency. A second potentiometer for controlling the clock oscillator frequency is coupled to a height adjustment member of the aperture, this frequency being used to clock delay shift registers such that the charging pulse may easily be made to occur at the appropriate time, irrespective of fluctuations of pressure, velocity, amplitude and frequency of the droplet forming generator. See U.S. Pat. No. 3,963,606, (Hogg) Col. 2, lines 23-37. Accordingly, Hogg represents a more automated version of the stroboscopic projection microscopic techniques discussed above.

Droplet forming characteristics in a perturbed stream have also been considered in connection with the art of ink jet printing. In the ink jet printing art, where discrete ink droplets formed in an ink jet stream are electrostatically directed to form characters on a recording surface, particular attention has been paid to establishing uniform droplet formation and charging characteristics. Since the charge imparted to any given droplet at its breakpoint is proportional to its surface area, i.e., the shape of that droplet at the breakpoint, and since even slight charge variations may produce erratic deflection characteristics, ink jet printing artisans have proposed various systems for producing an ink jet stream comprising uniformly shaped and uniformly charged droplets which will exhibit predictable down stream deflection behavior. These problems are complicated by the tendency of perturbed streams to form "satellites" which not only affect the charge imparted to preceeding or succeeding droplets, but also alter the volume of those droplets, thereby correspondingly affecting print uniformity.

In the ink jet printing art, numerous systems have been proposed for sensing the characteristics of a perturbed ink jet stream, either above or below the breakpoint of that stream. U.S. Pat. No. 3,907,429 (Kuhn, et al) discloses a method and device for detecting the velocity of droplets formed from a liquid stream. According to this disclosure, discrete droplets are directed between a pair of apertures and a light source which is strobed at a selected frequency and directed towards the apertures. By detecting the time between when a first of the apertures is blocked by a droplet in the stream as indicated by the light being broken during the strobe and the time when a second of the apertures is blocked by another droplet, when the light source is counted, the velocity of the droplets may be measured and a correction of the velocity made by changing the pressure of the manifolds supplying the liquid stream. In U.S. Pat. No. 3,769,627 (Stone) an ink jet printing system using ion charging of droplets is disclosed wherein a light source and photocell located downstream from the breakpoint of a perturbed stream is used to sense the passage of discrete droplets and to time delayed charges subsequently applied thereto. Stone states:

"Selective drop charging involves the induction of charges in the drop being formed by a surrounding charged electrode. The induced charge varies in accordance with the inducing voltage until the instant in time when the droplet physically separates from the stream. From that time on, the induced charged is trapped and remains with the drop. It is obvious, therefore that the charging process must be carefully synchronized with the timing of the drop break off. This involves the use of complex phasing control sensors and loops. This in turn, increases the cost of the equipment.

It is an object of this invention to provide an ink drop charging system which does not depend upon the synchronization of the charging with the break off time.

It is another object of this invention to produce an ink drop charging system, which charges drops after they break off from the ink jet stream." U.S. Pat. No. 3,769,627 (Stone), Col. 1, lines 18–35.

This method is accomplished by using the above-described photocell arrangement for the purpose of counting and synchronizing charges applied as discrete droplets pass a plurality of separate charging stations which respond to coded information applied to each station in synchronism with the passage of each drop.

As disclosed in U.S. Pat. No. 4,047,183 (Taub), efforts have also been made to control the formation and shape of droplets in an ink jet stream by sensing the surface wave profile of the continuous portion of the stream (upstream from the breakpoint) by illuminating that portion of the stream with a radiant energy source such as a laser. The surface wave profile produced by illuminating the stream is sensed to provide the fundamental and harmonic frequency components thereof, and a perturbation drive signal, the amplitude and relative phase of which is a function of the sensed frequency components, is provided for controlling the formation and shape of the droplets. After discussing the advantages and difficulties of controlling the break off geometry, particularly with the respect to the illumination of satellite formations, Taub discloses the practical desirability of measuring the ink jet stream upstream rather than downstream from the droplet break off point:

"The ideal time to sense the frequency, phase, and amplitude components of the ink jet stream for determining drop break off characteristics is at the precise time droplets are formed therefrom. This is usually impossible to achieve, however, since the droplets are normally formed inside the charged electrode. Therefore, according to the present invention, the drop break off characteristics are determined by sensing upstream of break off, rather than downstream as taught by the prior art. The continuous portion, that is, the portion just prior to break off of the stream is sensed to determine the break off characteristics. In response to the sensed characteristics, a piezoelectric drive signal is provided which controls droplet formation, and accordingly provides increased drop charging efficiency." U.S. Pat. No. 4,047,143 (Taub), Col. 4, lines 53–68.

Taub discloses a system wherein an ink jet manifold having a perturbation means such as a piezoelectric crystal emits a perturbed ink jet stream into charge electrode structures which are pulsed in "a well known manner" to selectively apply charge to the droplets. A source of radiant energy, which may comprise a helium-neon laser, emits radiant energy focused on the continuous portion of the jet "just prior to the jet entering the charged electrode structure". "Since the ink is opaque, a shadow is formed" which is imaged through a lens onto a substrate which has a slit formed therein. The shadow formed thereby represents the surface wave profile of the jet which is a representation of the respective amplitudes and relative phases of fundamental and harmonic frequencies. Taub states:

"The light passing through the slit 44 is influenced by the wave passing a given point on the perimeter of the jet, and accordingly is a representation of the frequency components of the jet at this particular point, as well as being indicative of the shape of a given droplet when it breaks-off downstream. It is necessary to make this slit somewhat larger than the largest diameter to be measured, typically the drop diameter, so that the clipping of the wave form does not occur, as well as preventing the generation of spurious diffraction effects. A narrow band pass filter 48, which has a band pass on the order of 100 A centered in the laser wavelength, is used so measurements may be made in room light. The light passed by the filter 48 is then transmitted to a photomultiplier tube 50 which measures the intensity of the light. Therefore, the output voltage of the photomultiplier tube 50 is proportional to the diameter of the jet blocking the slit, which is to say, to the local diameter of the jet at the point being probed . . . it is to be appreciated that the signal output . . . may be applied to analyzing means 80 by other timing means such as a stepping motor, or alternatively may be applied concurrently to inputs of devices 82, 84 and 86, rather than in the time sequence described." U.S. Pat. No. 4,047,183. See Col. 6, lines 27–68, Col. 7, lines 1–26.

In Taub's preferred embodiment, the output signal so obtained is conditioned to control the fundamental and harmonic frequencies applied to the piezoelectric perturbation means for controlling the droplet formation and shape of droplets produced by the ink jet stream.

For other disclosures of ink jet printing systems using optical sensors, see IBM Technical Disclosure Bulletin Volume 16, No. 12, May 1974, Page 3877–8, entitled "Feedback for Synchronized Pressure Jet Using Optical Sensor"; and IBM Technical Disclosure Bulletin, Vol. 16, No. 3, Aug. 1973, Page 880, entitled "Phase Detection On Ink Jet Droplets".

For other disclosures relating to various ink jet printing synchronization systems, please refer to U.S. Pat. No. 4.025,926 (Fujimoto, et al) entitled, "Phase Synchronization For Ink Jet System Printer"; U.S. Pat. No. 4,045,770 (Arnold, et al) entitled, "Method and Apparatus For Adjusting The Velocity Of Ink Drops In An Ink Jet Printer"; U.S. Pat. No. 3,953,860 (Fujimoto, et al) entitled, "Charge Amplitude Detection For Ink Jet System Printer"; U.S. Pat. No. 3,761,941 (Robertson) entitled, "Phase Control For A Drop Generating and Charging System"; U.S. Pat. No. 3,836,912 (Ghougasian, et al) entitled, "Drop Charge Sensing Apparatus For Ink Jet Printing System"; U.S. Pat. No. 3,982,251 (Hochberg) entitled, "Method and Apparatus For Reducing Information On a Recording Medium"; U.S. Pat. No. 3,878,519 (Eaton) entitled, "Method and Apparatus For Synchronizing Droplet Formation In A Liquid Stream".

For other patents disclosing particle or flow sorting systems, please see U.S. Pat. No. 3,941,479 (Whitehead) entitled, "Use Of Modulated Stimulus To Improve Detection Sensitivity For Signals From Particles in A Flow Chamber"; U.S. Pat. No. 3,851,169 (Faxvog) entitled, "Apparatus For Measuring Aerosol Particles"; and U.S. Pat. No. 3,910,702 (Corll) entitled, "Apparatus For Detecting Particles Employing Apertured Light Emitting Device".

SUMMARY OF THE INVENTION

The present invention provides a novel method for synchronizing the phase of droplet charge pulses in electrostatic flow sorting systems so that those charge pulses may be applied in a preselected phase with respect to the phase of droplet formation at the droplet breakpoint of a perturbed laminar flow stream. In electrostatic flow sorters, it is necessary to initiate the charging of droplets at a specific point in time with respect to formation of droplets. In this manner appropriate charges are induced in the target droplets, but not in their adjacent relatively uncharged droplets. Typically, the charging of droplets is carried out via the application of charge pulses that are applied one half droplet period time before the droplet breaks off, with the charge pulse lasting up to one half droplet period after the droplet breaks off. In this manner, the desired full charge is normally induced upon the droplet at the time of break off. Occasionally, however, the occurance of satellites between droplets suggests the setting of a different charge initiation time for proper droplet charging. Unlike the prior art, where the transducer waveform is utilized as the reference waveform with respect to which charge pulses are initiated, the system of the present invention continuously monitors droplet formation shape at the breakpoint, and produces a proportional output signal with respect to which the droplet charging pulses can be continuously phased. In this manner, continuous and automatic adjustment of the phase of the charge pulse automatically compensates for flow rate and fluid velocity variations. Accordingly, droplet formation phase variations produced as a result of variations in flow rate, surface tension, viscosity, temperature, etc. will not affect the synchronization of the charge pulse with the phase of droplet formation.

Accordingly, a primary object of the present invention is the provision of an apparatus and method for synchronously charging droplets in an electrostatic flow sorting system in preselected phased relationship to the formation of droplets at the breakpoint of a perturbed laminar flow stream. This and other objects of the present invention will become apparent from the following more detailed description.

BRIEF DESCRIPTION OF THE DRAWINGS

FIG. 1 is a diagrammatic block drawing of the preferred embodiment of the present invention.

DETAILED DESCRIPTION OF THE DRAWINGS

Although specific forms of the invention have been selected for illustration in the drawings, and the following description is drawn in specific terms for the purpose of describing these forms of the invention, this description is not intended to limit the scope of the invention which is defined in the appended claims.

The present invention provides a novel method for phasing the application of charge pulses to the formation of droplets at a droplet formation point in a perturbed laminar flow stream of an electrostatic particle sorting system. FIG. 1 is a diagrammatic illustration of the preferred embodiment system of the present invention. For purposes of simplicity in illustration, that portion of the system establishing the fluid flow of the core stream and sheath stream portions has been omitted from the drawing, as has the particle sensing means which is normally oriented slightly above or below the orifice from which the perturbed laminar flow stream is released. In FIG. 1, a perturbed laminar flow stream 10 is seen jetting from orifice 12. This perturbed laminar flow stream 10 was created by a flow means 11 for establishing the flow of a continuous particle containing stream comprising at least a particle containing core stream portion and a surrounding sheath stream portion. This stream defines a particle sensing point, such as particle sensing point 14, which may be located substantially adjacent to orifice 12. Although not illustrated in the drawings, optical detection means for optically detecting said particles at least at said particle sensing point are provided, and may be of the laser type heretofore known to the art for this purpose. A transducer 16 perturbs the orifice, and thus the laminar flow stream travelling therethrough with at least a preselected frequency and amplitude to cause the stream to form a break point or droplet formation point at which said stream 10 becomes a series of discrete droplets.

A droplet charging system 18 is provided for relatively charging selected ones of said droplets as they are formed at said break point. This is normally accomplished by inducing a relative charge within the stream at the time of discrete droplet formation such that that induced charge becomes fixed in that droplet at the time of break off. Since it is desired to selectively charge droplets containing particles which have been sensed by the optical detection means, it is important to induce the desired state of charge on the selected particle containing droplet, while insuring that preceeding or subsequent non-particle containing droplets do not receive substantial induced charges. Similarly, it is important to synchronize the phase of the charging pulse so that a preselected amplitude of induced charge will be produced for the target droplet, and to insure that an out-of-phase application of that charge does not inadvertently result in a partially charged target droplet. Accordingly, synchronization means is provided for performing said relative charging at a preselected time with respect to the phase of formation of said discrete droplets at said breakpoint. This synchronization means comprises a sheath sensing means for sensing the light scatter and extinction of said stream at a sheath sensing point which is subsequent to the locus of said perturbation, and for producing a surface character output signal which is proportional thereto. In the preferred embodiment, the sheath sensing means comprises a focused light source 20 which is preferably a helium neon laser, but which may also be a light emitting diode, laser diode, or other conventional light source. The focused light source is focused on the laminar flow stream 10 utilizing conventional optic lenses, such as using an FC-200 Ortho Instruments lens assembly, such as that used to focus a particle detecting laser upon the core stream of an electrostatic flow sorter. Axially aligned on the opposite side of the flow stream 10 from focused light source 20 is a detector 22 of incident optical energy which produces, after appropriate signal conditioning via signal conditioning circuits 24, a surface character output signal which is proportional to the surface character of the shape of the sheath stream portion of the fluid column passing the focused beam. In accordance with the preferred embodiment of the present invention, the signal conditioning circuits utilized for conditioning the detector 22 output may be conventional amplifiers and filters to amplify and improve the signal to noise ratio of the detector output. The surface character output signal is sensed by a charge pulse phase generator 26 which analyzes at least the phase of said surface character output signal. Since the phase of the surface character output signal corresponds to the phase of droplet formation at the sheath sensing point, by providing a charge pulse generator for providing a charge pulse in preselected phased relationship to the phase of said surface character output signal, the charging of the droplets at the droplet formation point will be synchronized. In order to insure that the synchronization of the droplet charging pulse is flow rate, viscosity, surface tension, and temperature invariant, it is necessary to insure that the sheath sensing point remain aligned precisely at the droplet formation point. This is accomplished by sensing and analyzing the surface character output signal of the sheath sensing means and by using an error signal generator 30 and a reference position setting 32 (preferably a breakpoint reference position setting) for the purpose of generating an error signal when the sheath sensing point is not aligned with the droplet formation or break point of the perturbed flow stream 10. This error signal actuates a driver 34 which acts on an electromechanical positioning system 36 for mechanically shifting the sheath sensing point in response to the aforementioned error signal. The sheath sensing point shift means accordingly causes the sheath sensing point to track the break-point, or at least at a preselected position relative to the breakpoint.

In the event that a particular particle has been sensed by the optical detection means, a droplet charge command means 38 responsive thereto will provide a timed delay droplet charge command to the charge pulse generator 28. This enables the synchronous application of the charge pulse by the charge pulse generator 26.

In view of the above, it will be seen that the apparatus and method of the present invention enable the synchronous application of droplet charging pulses in any desired phased relationship with the formation of droplets at the droplet formation point of a perturbed laminar flow stream, regardless of variations in flow rate, surface tension, viscosity, temperature, or other factors which might otherwise affect the phase of droplet formation at that droplet formation point.

It will be understood that various changes in the details, materials and arrangement of parts which have been herein described and illustrated in order to explain the nature of this invention may be made by those skilled in the art within the principle and scope of the invention as expressed in the following claims. As used herein, "perturbed" or "perturbation" is meant to include not only mechanical/vibratory methods for creating discontinuities in the stream, but also discontinuities which are induced by other means such as alteration of stream surface tension, for example, by electrical, thermal, or optical means. Likewise, periodic or aperiodic perturbations are meant to be included.

It will be understood that the "Abstract of the Disclosure" set forth above is intended to provide a non-legal technical statement of the contents of the disclosure in compliance with the Rules of Practice of the United States Patent and Trademark Office, and is not intended to limit the scope of the invention described and claimed herein.

What is claimed is:

1. An electrostatic particle sorting system, comprising:
(a) flow means for establishing the flow of a continuous particle containing stream comprising at least a particle containing core stream portion and a surrounding sheath stream portion, said stream having a particle sensing point defined therealong;
(b) optical detection means for optically detecting said particles at least at said particle sensing point;
(c) perturbation means for perturbing said stream with at least a preselected frequency and amplitude to cause said stream to form a break point at which said stream becomes a series of discrete droplets;
(d) droplet charging means for relatively charging selected ones of said droplets as they are formed at said break point;
(e) synchronization means for performing said relative charging at a preselected time with respect to the phase of formation of said discrete droplets at said break point, said synchronization means comprising:
(i) sheath sensing means for sensing at least the light scatter of said stream at a sheath sensing point therealong subsequent to said perturbation, and for producing a surface character output signal which is proportional thereto; and
(ii) surface character analysis means for analyzing at least the phase of said surface character output signal;

and wherein said droplet charging means comprises charge pulse generation means for providing a charge pulse in a preselected phased relationship to said phase of said surface character output signal.

2. The invention of claim 1 wherein said droplet charging means further comprises droplet charge command means responsive to said optical detection means for providing a time delayed droplet charge command to said charge pulse generation means.

3. The invention of claim 1 wherein said sheath sensing means further comprises means for sensing the extinction of said light caused by said stream at said sheath sensing point.

4. The invention of claim 1 wherein said droplet charging means further comprises droplet charge command means responsive to said detection means for providing a time delayed droplet charge command to said charge pulse generation means.

5. The invention of claim 1 wherein said synchronization means further comprises sheath sensing point shift means for establishing and maintaining said sheath sensing point at a preselected position with respect to said breakpoint.

6. The invention of claim 5 wherein said sheath sensing point shift means further comprises error signal generator means for comparing said surface character output signal to a preselected reference signal setting and for producing an error signal proportional to compared differences therebetween.

7. The invention of claim 6 wherein said sheath sensing point shift means further comprises a driver and electromechanical positioning means for shifting said sheath sensing means in response to said error signal to said preselected point with respect to said break point.

8. An electrostatic particle sorting method comprising the steps of:
(a) establishing the flow of a continuous particle containing stream comprising at least a particle containing core stream portion and a surrounding sheath stream portion, said stream having a particle sensing point defined therealong;
(b) optically detecting said particles at least at said particle sensing point;
(c) perturbing said stream at a preselected perturbation point with at least a preselected frequency and amplitude to cause said stream to form a breakpoint at which said stream becomes a series of discrete droplets;
(d) relatively charging said selected ones of said droplets as they are formed at said breakpoint; and
(e) synchronizing said relative charging at a preselected time with respect to the phase of formation of said discrete droplets at said breakpoint, said synchronization step comprising the steps of:
(i) sensing at least the light scatter characteristics of said stream at a sheath sensing point defined therealong subsequent to said perturbation point, and generating a surface character output signal which is proportional thereto; and
(ii) analyzing said surface character output signal at least to determine the phase of said surface character output signal; and
(f) generating a charge pulse in a preselected phased relationship with respect to the phase of the surface character output signal detected in step (e)(ii) above.

9. The invention of claim 8 wherein said step of relatively charging said droplets further comprises the step of time delaying degeneration of a droplet charge command, delay the application of said charge pulse, said charge command being responsive to said optical detection of particles in said stream.

10. The invention of claim 8 wherein said step of sensing at least the light scatter characteristics of said stream further comprises the step of sensing the light extinction characteristic of said stream.

11. The invention of claim 8 wherein said step of relatively charging said droplets further comprises the step of time delaying degeneration of a droplet charge command, delay the application of said charge pulse, said charge command being responsive to said detection of particles in said stream.

12. The invention of claim 8 wherein said synchronization step further comprises the step of establishing and maintaining said sheath sensing point at a preselected position with respect to said breakpoint.

13. The invention of claim 12 wherein said step of establishing and maintaining said sheath sensing point further comprises the steps of comparing said surface character output signal to a preselected reference signal setting and generating an error signal proportional to the compared differences therebetween.

14. The invention of claim 13 wherein said step of establishing and maintaining said sheath sensing point further comprises the step of moving said sheath sensing point relative to said breakpoint in proportional response to said error signal.

15. An electrostatic particle sorting system, comprising:
(a) flow means for establishing the flow of a continuous particle containing stream comprising at least a particle containing core stream portion and a surrounding sheath stream portion, said stream having a particle sensing point defined therealong;
(b) detection means for detecting said particles at least at said particle sensing point;
(c) perturbation means for perturbing said stream with at least a preselected frequency and amplitude to cause said stream to form a break point at which said stream becomes a series of discrete droplets;
(d) droplet charging means for relatively charging selected ones of said droplets as they are formed at said break point;
(e) synchronization means for performing said relative charging at a preselected time with respect to the phase of formation of said discrete droplets at said break point, said synchronization means comprising:
(i) sheath sensing means for sensing at least the light scatter of said stream at a sheath sensing point therealong subsequent to said perturbation, and for producing a surface character output signal which is proportional thereto; and
(ii) surface character analysis means for analyzing at least the phase of said surface character output signal;
and wherein said droplet charging means comprises charge pulse generation means for providing a charge pulse in a preselected phased relationship to said phase of said surface character output signal.

16. An electrostatic particle sorting method comprising the steps of:
(a) establishing the flow of a continuous particle containing stream comprising at least a particle containing core stream portion and a surrounding sheath stream portion, said stream having a particle sensing point defined therealong;
(b) detecting said particles at least at said particle sensing point;
(c) perturbing said stream at a preselected perturbation point with at least a preselected frequency and amplitude to cause said stream to form a breakpoint at which said stream becomes a series of discrete droplets;
(d) relatively charging said selected ones of said droplets as they are formed at said breakpoint; and
(e) synchronizing said relative charging at a preselected time with respect to the phase of formation of said discrete droplets at said breakpoint, said synchronization step comprising the steps of:
(i) sensing at least the light scatter characteristics of said stream at a sheath sensing point defined therealong subsequent to said perturbation point, and generating a surface character output signal which is proportional thereto; and
(ii) analyzing said surface character output signal at least to determine the phase of said surface character output signal; and
(f) generating a charge pulse in a preselected phased relationship with respect to the phase of the surface character output signal detected in step (e)(ii) above.

* * * * *